US005866343A

United States Patent [19]
Blom et al.

[11] Patent Number: 5,866,343
[45] Date of Patent: Feb. 2, 1999

[54] ENERGETICALLY FAVORABLE BINDING SITE DETERMINATION BETWEEN TWO MOLECULES

[75] Inventors: Nico Blom, Pointe Claire; Jurgen Sygusch, Montreal, both of Canada

[73] Assignee: Université de Montréal, Montreal, Canada

[21] Appl. No.: 837,967

[22] Filed: Apr. 15, 1997

[51] Int. Cl.[6] ............................ G01N 33/53; G06F 17/14
[52] U.S. Cl. ............................................. 435/7.1; 364/578
[58] Field of Search ................................... 364/496, 578; 436/501; 435/7.1

[56] References Cited

U.S. PATENT DOCUMENTS

| 5,025,388 | 6/1991 | Cramer et al. . |
| 5,583,973 | 12/1996 | DeLisi et al. . |
| 5,642,292 | 6/1997 | Itai et al. . |

OTHER PUBLICATIONS

Brian K. Shoichet and Irwin D. Kuntz, "Matching chemistry and shape in molecular docking", Protein Engineering, vol. 6 No. 7, pp. 723–732, 1993.

Peter Kollman, "Free Energy Calculations: Applications to Chemical and Biochemical Phenomena", Chem. Rev. 1993, 93, pp. 2395–2417.

P.J. Goodford entitled "A Computational Procedure for Determining Energetically Favorable Binding Sites on Biologically Important Macromolecules", J. Med. Chem. 1985, 28, pp. 849–857.

N.C.J. Strynadka et al., "Molecular docking programs successfully predict the binding of a β–lactamase inhibitory protein to TEM–1 β–lactamase" Nature Structural Biology, vol. 3, No. 3, pp. 233–239, Mar. 1996.

Ephraim Katchalski–Katzir et al., "Molecular surface recognition: Determination of geometric fit between proteins and their ligands by correlation techniques", Proc. Natl. Acad. Sci. USA, vol. 89, pp. 2195–2199, Mar. 1992.

Robert W. Harrison et al., "The Fourier–Green's function and the rapid evaluation of molecular potentials", Protein Engineering, vol. 7, No. 3, pp. 359–369, 1994.

(List continued on next page.)

*Primary Examiner*—Lora M. Green
*Assistant Examiner*—Joseph W. Ricigliano
*Attorney, Agent, or Firm*—Hamilton, Brook, Smith & Reynolds, P.C.

[57] ABSTRACT

A 'docking' method based on finite grid forcefield sampling makes use of fast evaluation of interaction energies between molecules, such as macromolecules and ligands. The forcefield used to calculate interaction energies utilizes a potential energy function composed of a 1/r dependent electrostatic term and a (6–12) Lennard-Jones term for Van der Waals interactions. Successful prediction of ligand position and determination of ligand-protein interaction enthalpy is done by mapping potential energy field components of one of the molecules onto a energy field component grids, and mapping interaction field components of another of the two molecules onto interaction component grids. By calculating a correlation between each potential energy field component grid and each interaction field grid, a plurality of grids of molecule binding energy values is obtained which represent a binding energy of the two molecules in the given relative rotation between the molecules for each relative translational positions in space between the molecules. At least one maximum of the binding energy values is determined and the relative translational positions for the maximum binding energy values are recorded. By rotating at least one of the molecules according to each relative rotation in a range of rotation, and by repeating the mapping for the rotated molecule and subsequently repeating the calculating and determining for each of the relative rotations, it is possible to select an energetically favorable one of the relative rotations and the relative translational positions to generate a position value for an energetically favorable binding site between the two molecules.

24 Claims, 3 Drawing Sheets

OTHER PUBLICATIONS

Ilya A. Vakser, "Protein Docking for low-resolution structures", Protein Engineering, vol. 8, No. 4, pp. 371–377, 1995.

Nick S. Blom et al., "High Resolution Fast Quantitative Docking Using Fourier Domain Correlation Techniques", PROTEINS: Structure, Function, and Genetics 27:493–506 (1997).

Katchalski–Katzir. E., et al., (Mar.1992) Molecular surface recognition: Determination of geometric fit between proteins and their ligands by correlation techniques. Proc. Natl. Sci. USA., 89: 2195–2199.

Harrison, R.W., et al., (Mar. 1994) The urier–Green's function and the rapid evolution of molecular potentials. Protein Eng. 7: 359–369.

FIG_4

ENERGETICALLY FAVORABLE BINDING SITE DETERMINATION BETWEEN TWO MOLECULES

This application includes a microfiche Appendix containing a computer program listing.

FIELD OF THE INVENTION

The present invention relates to a method for generating a position value for an energetically favorable binding site between two molecules. More particularly, the invention relates to a computational tool for the determination of energetically favorable binding sites in macromolecules and further, to a high resolution fast quantitative docking determination tool using Fourier domain correlation techniques.

BACKGROUND OF THE INVENTION

The development of computation tools for the determination of energetically favorable binding sites in macromolecules, referred to as "docking", has been of considerable interest during the past decade. These tools have been introduced to assist structure-based drug design. The approaches fall into two main categories, namely, qualitative and quantitative methods. Qualitative methods are restricted primarily to calculations based on shape, complementarity and consist of finding the best fit between two shapes. A computer program called "Dock" exemplifies this approach and has been described in the paper authored by B. K. Shoichet and I. D. Kuntz entitled "Matching chemistry and shape in molecular docking", which appeared in Protein Engineering, 7:723–732, 1993. Quantitative methods are based primarily on energy calculations seeking to determine the global minimum energy of the ligand binding interaction with the protein target. This approach is described in the paper by P. A. Kollman entitled "Free energy calculations: applications to chemical and biochemical phenomena", published in Chem. Rev. 93:2395–2417, 1993. Hybrid methods also exist in the form of calculating interaction energy between a given protein and small molecular fragments which are then assembled based on shape, complementarity criteria to form new molecules. This approach is described in the paper by P. A. Goodford entitled "Computational procedure for determining energetically favorable binding sites on biologically important molecules", published in J. Med. Chem, 28:849–857, 1985. More recently, a successful prediction was achieved in describing the binding of β-lactamase inhibitor protein with TEM-1 β-lactamase by employing both quantitative and qualitative methods as well as a combination thereof. This approach is documented in the paper by N. Strynadka et al entitled "Molecular docking program successfully predict the binding of β-lactamase inhibitory protein to TEM-1 β-lactamase", published in Nature Struct. Biol, 3(3):233–239, 1996.

When developing a computational tool for the determination of favorable binding sites in molecules, according to the quantitative methods, it is possible to simulate intermolecular movement by computing intermolecular forces to determine a preferred "docking" site between the molecules. It is also possible to calculate the energy of interaction between the two molecules to determine as the best binding site those sites which have the most favorable or minimum potential energy. The predictive accuracy of any quantitative method is limited by the resolution or precision of the model. In most calculations, a grid is used onto which the molecule structures are mapped. This mapping takes place with or without some kind of transfer function, e.g. a 1/r-function in the case of electrostatic potential description. The calculation of the interaction between the two molecules, such as calculating the potential energy between the two molecules, must be done for each relative position of the two molecules, namely, each relative translational position and each rotational orientation between the two molecules. Since the amount of computation is extremely high, the prior art approach has been to select a moderate grid resolution before performing a calculation of favorable binding sites between molecules.

SUMMARY OF THE INVENTION

It is an object of the present invention to make use of correlation between a potential grid representing one molecule and an interaction field grid representing another molecule to obtain for each selected relative rotation between the two molecules a potential energy representing a binding energy of the two molecules for relative translational positions in space between the two molecules. Using a single complex correlation calculation for each relative rotation between the two molecules, the resulting grids can be scanned to obtain the most energetically favorable binding site between two molecules. By using a grid resolution in the range of 0.25 Å–0.45 Å, it has been found that at such high resolution the correlation technique by convolution of two grids representing the two molecules provides very acceptable quantitative results for molecule binding energy for all relative translational positions in space between the two molecules.

According to the invention, there is provided a method for generating a position value for an energetically favorable binding site between two molecules, comprising the steps of: a) obtaining potential energy structural data for each atom site in the molecules; b) selecting a grid resolution corresponding to a sampling grid size substantially smaller than an average distance between bonded atoms in the molecules; c) selecting a range of relative rotations between the two molecules; d) mapping a plurality of potential energy field components of one of the molecules onto a corresponding one of a plurality of energy field component grids having the resolution with one molecule at a predetermined rotation and position, wherein each grid point of the component grids has a potential energy value interpolated from the potential energy structural data; e) mapping a plurality of interaction field components of another of the molecules onto a corresponding one of a plurality of interaction component grids having the resolution with the other molecule at a predetermined rotation and position, the interaction component corresponding to coefficients of a forcefield between the molecules, wherein each grid point of the component grids has an interaction value interpolated from the potential energy structural data; f) calculating a correlation between each potential energy field component grid and each interaction field component grid to obtain a grid of molecule binding energy values representing a binding energy of the two molecules in the relative rotation for relative translational positions in space between the molecules; g) determining at least one maximum of the binding energy values and recording the relative translational positions for the maximum binding energy values; h) rotating at least one of the molecules according to each relative rotation in the range, repeating the step of mapping for the at least one of the molecules and subsequently repeating the steps (f) and (g) of calculating and determining for each relative rotation; and i) selecting an energetically favorable one of the relative rotations in the range and the relative translational positions based on the maximum binding energy values to generate the position value for an energetically favorable binding site between the two molecules.

As can be appreciated, since only one molecule needs to be rotated relative to the other, the map of one of the molecules can be used repeatedly while the map of the second molecule can be recalculated for each new rotational position. Since the interaction field components are easier to map, it is preferred that only the interaction component grids be remapped for each new rotation. Also preferably, the preferred transform for carrying out the correlation is the discrete Fourier transform.

Preferably, the potential energy field components consist of the electrostatic potential which is based on Coulomb's law and varies as a function of $1/r$, a second component for the first Van der Waals term A which varies as a function of $1/r^{12}$ and a third component grid for the second Van der Waals term B which varies as a function of $1/r^6$. As can be appreciated, selection of the Van der Waals terms is a matter of selection of a preferred model and other models other than the Lennard Jones 6–12 potential energy description may be used. The result of the correlation for each field component must be summed with the results of the other components in order to obtain a total binding energy of the two molecules for the given relative rotation and for each relative translational position in space provided within the grid.

It is preferred according to the invention to record a plurality of most energetically favorable maximum binding energy values. In order to select the most energetically favorable binding site between two molecules, it is preferred to apply Boltzmann's statistics in order to determine the probabilities of occupying the various most energetically favorable binding energy states in order to determine which state is most probable and generate as the position value the position value corresponding to the relative position between the two molecules corresponding to the most probable binding energy value.

Also preferably, the method may be used at a plurality of resolutions in order to accommodate ease of computation. For example, a first stage of generating the best position value or best position values at a grid resolution of 0.4 Å may be confirmed by proceeding with a 0.25 Å grid resolution in which the range of relative rotations between the two molecules are centered closely around each of the relative rotations determined at the initial lower resolution. Since higher resolution requires greater memory and manipulation of data during calculation, the grid dimensions at the higher resolution may be selected knowing in advance what grid dimensions will accommodate the anticipated result while working with smaller dimensions of grids.

BRIEF DESCRIPTION OF THE DRAWINGS

The invention will be better understood by way of the following detailed description of a preferred embodiment of the invention in which.

DETAILED DESCRIPTION OF THE PREFERRED EMBODIMENT

In the preferred embodiment, the molecules whose most energetically favorable binding site position values to be generated are macromolecules, namely, a protein and a ligand. The protein typically has a very large number of atoms in its structure in the order of 5000 or greater. The ligand is typically between 1–25% of the size of the protein.

Figure 1:
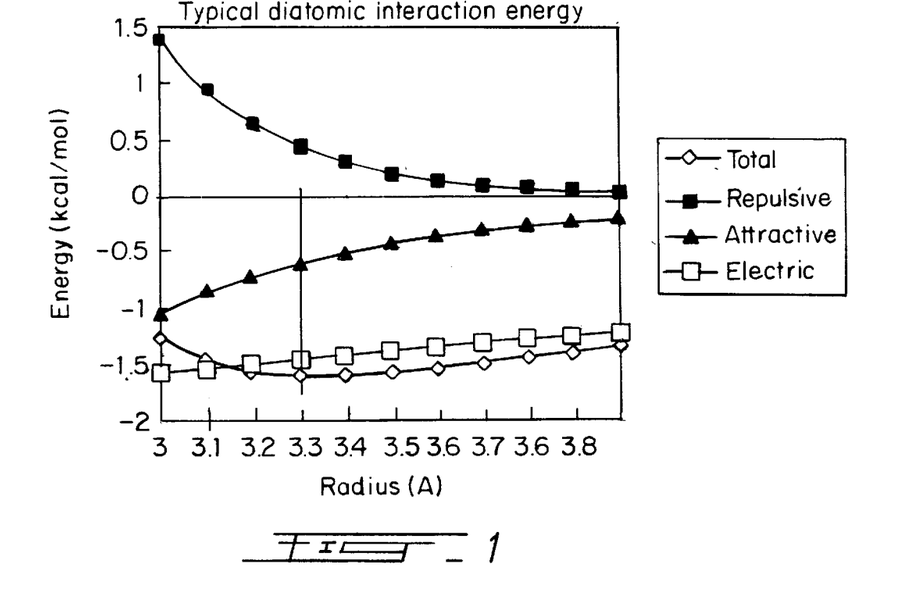
FIG. 1 shows an exemplary energy vs. radius diagram for the total potential energy of an atom in a molecule in proximity with another atom of another molecule in which the electrostatic potential, repulsive $1/r^{12}$ Van der Waals potential and the attractive $1/r^6$ potential are also shown separately and the maximum negative binding energy trough can be seen, according to the prior art.
Figure 2:
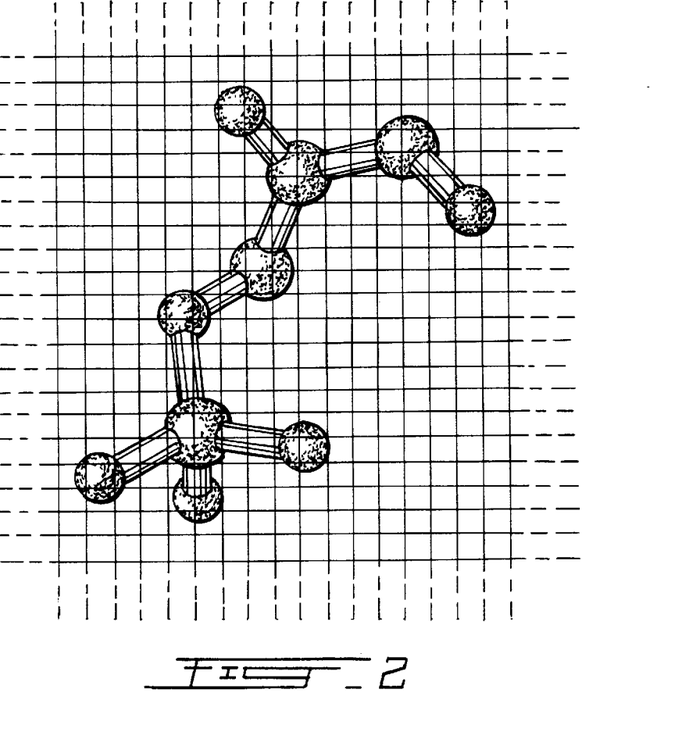
FIG. 2 is a two-dimensional projection of dihydroxy acetonephosphate superimposed on a grid having a resolution of 0.4Å.

The potential energy of the system consisting of the protein and ligand is calculated by determining the potential energy field created by the protein and then calculating the potential energy resulting from the contribution of each atom in the ligand for a particular position in space within the potential energy field of the protein. The potential energy is calculated using three basic terms. The first term is the electrostatic potential. This results from an electrostatic charge at a particular atom within the ligand interacting with the electrostatic field potential created by the molecule. Such potentials are greater in polar or ionic molecules. The second and third potential energy terms come from the Van der Waals potentials. In the preferred embodiment, the 6–12 Lennard Jones potential is used. As illustrated in FIG. 1, the combination of the three potential energy terms may lead to a potential energy minimum (maximum binding energy) as a particular radial distance. Potential terms can be extended by an explicit term for hydrogen bond interaction.

For the chosen protein and the chosen ligand, data concerning static charge at the atom sites in the molecules as well as the coefficients for the Van der Waals forces are obtained from existing databases. Such potential energy structural data is originally determined empirically and/or by theoretical model calculations. Next, a grid resolution corresponding to a sampling grid size substantially smaller than an average distance between atoms in the molecules is selected. It has been found that a sampling grid size of 0.4 Å provides, in most cases, sufficiently high resolution to obtain good results for protein ligand pairs. A grid resolution of 0.25 Å, while computationally more intensive, has been found to provide substantially more accurate results. While it would be possible to select a grid resolution which is higher for the $1/r^{12}$ component than for the $1/r^6$ component, and even then a lesser resolution for the $1/r$ component of the potential energy field components, the individual component energy correlation calculation would be faster for the lower resolution grids, however, there would result the complication that addition for each point in space of the total binding energy would require calculating an interpolated value from the lower resolution grids to obtain binding energy values with respect to each point in the higher resolution grid.

Once the grid resolution is selected, each potential energy field component of one of the molecules, in the preferred embodiment the protein, is mapped onto a corresponding energy field component grid. This typically involves calculating for each grid point the potential energy field created by each atom site in the protein and summing all potentials to obtain the field potential. Since this step of mapping may only be carried out once, the effect of every atom site in the protein may be taken into account and all of the computation time required may be taken. For atoms very close to a grid point, where computational errors can result from selection outside the representation range of numbers in a computer, an arbitrary high value for their contribution to the potential field is taken. The relative spatial coordinates of each atom site for the protein and for the ligand are known from the structural data obtained from existing databases, or from predicted structural data.

The ligand being generally, but not necessarily, a much smaller molecule is easier to map onto the grid. In the preferred embodiment, for the ligand, the potential energy field components are not mapped onto the grid but rather the interaction field components are mapped onto the grid. The interaction field components relate to the charge quantities in the case of the electrostatic potential and the Van der Waals coefficients in the case of the Van der Waals potentials. For each atom site, the coefficients associated therewith are mapped onto the grid points surrounding each atom site in virtual space. The interpolation method for such mapping may be trilinear or a Gaussian distribution. In the case of a Gaussian distribution, each atom site has coefficients which are mapped onto a block of 5×5×5 grid elements. For each grid element, the contribution of each atom is calculated using the Gaussian distribution function. In particular, for the $1/r^6$ and $1/r^{12}$ components, best results are obtained using a Gaussian interpolation. As can be appreciated, the calculation of the values for the interaction field grid relating to the ligand involves carrying out a series of simple calculations with respect to each atom site in the ligand. The interaction component grids are built up for the particular rotational orientation of the ligand within the grid space by calculating the interaction field components for all of the atom sites in the ligand.

Since the potential energy field grids and the corresponding interaction field component grids have the same grid resolution and grid size, a correlation between the two grids may be calculated. In the preferred embodiment, the discrete Fourier transform using a fast Fourier transform method is applied to each grid. The two transformed grids are then multiplied using element by element multiplication to obtain an intermediate product grid, and then the intermediate product grid is subjected to an inverse fast Fourier transform to obtain a grid representing for each point in the grid a binding energy for each component for each translational position in space between the protein and the ligand. By summing the resulting component grids for the binding energies, a single total binding energy grid is obtained. The total binding energy grid is scanned to determine a maximum binding energy value for the particular rotation of the ligand. As can also be appreciated, if an atom site happens to fall directly on a grid point as a result of the virtual rotation, the computational accuracy is not compromised. For this reason, it is further preferred to rotate the molecule whose interaction field components are being calculated and mapped onto the grid rather than rotating the molecule whose potential energy field components are being mapped. The method described thus far is carried out for every conceivable relative rotation between the protein and the ligand. Normally, this would be all orientations unless some prior knowledge of the molecule system is known. In a parallel computer system, the mapping of the interaction field components of the ligand to produce the grids, the calculation of the forward and inverse Fourier transforms to obtain the correlation result and adding of the component grids to obtain maximum binding energy values could all be done as independent tasks. The most memory and computation intensive component is, of course, the correlation calculation which could be carried out using a vector processor.

Figure 3:
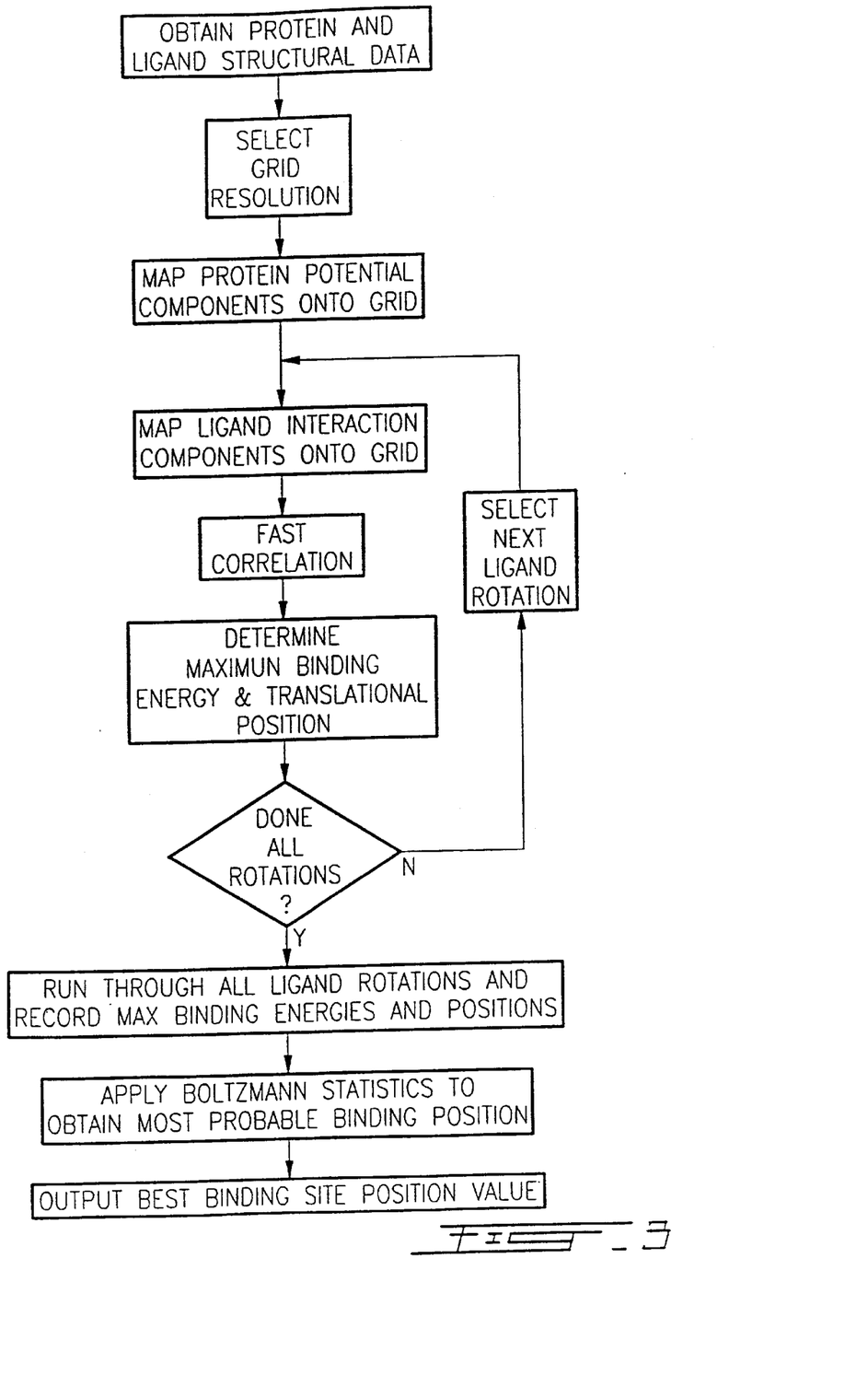
FIG. 3 is a flow diagram illustrating the method steps according to the preferred embodiment.
Figure 4:
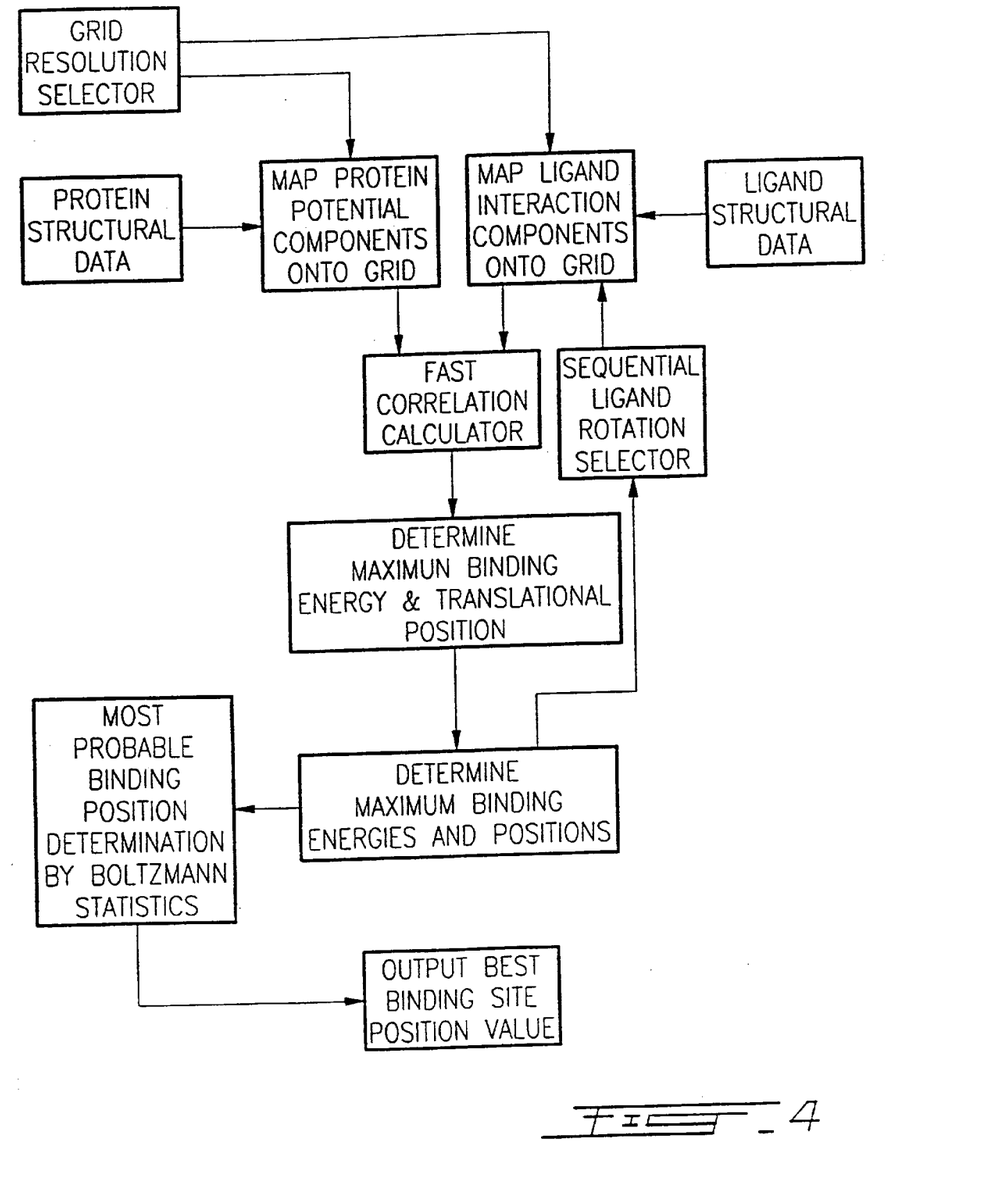
FIG. 4 is a block diagram of the position generator system according to the preferred embodiment.

As illustrated in FIG. 3, it is possible to carry out the above method initially at a course resolution, for example, at a sampling grid size of 0.4 Å only to select one or more most energetically favorable relative rotations and then repeat the method selecting a small solid angle around each most energetically favorable relative rotation, i.e. the rotation of the ligand, to determine at a resolution of, for example, 0.25 Å, what the exact maximum binding energy value is at each such rotational position in order to determine, based on the most energetically favorable binding energy value, the position value at the higher grid resolution. Also, when attempting to distinguish between a plurality of most energetically favorable maximum binding energy values, Boltzmann probabilities of occupying energy states corresponding to the most energetically favorable binding energy values can be calculated in order to select the most probable favorable binding energy value and generate as the position value the position value of the ligand corresponding to this maximum binding energy value. In the case that a few energetically favorable maximum binding energy values are the result of the above method and there is some uncertainty as to which binding energy value represents the likely binding site between the protein and the ligand, the method may be repeated following remapping of the interaction potential field components with the ligand being randomly shifted and rotated in space. The same rotations of the ligand are applied as before in order to obtain another set of maximum binding energy values having different computational error components. This procedure is repeated until agreement for the maximum binding energy value is obtained independently of the ligand starting position, greater confidence may be had in the resulting position value.

As can be appreciated, the above method presumes that the molecules are rigid and are not subjected to outside forces. The change in ligand shape in the dynamical interaction between two molecules can be considered as subsequent coordinate sets of the ligand and the method can be carried out for each different coordinate set of the ligand to determine the position value for the energetically favorable binding site for each coordinate set of the ligand, and as a result, determine what is the most likely dynamical docking configuration of the protein ligand system.

Treatment of the dynamical motion of the protein can be interpreted as subsequent evaluations of the binding energies each using a different conformation of the protein. It can be appreciated that such an approach, though valid, is inefficient from the point of view of computation time, since, expectedly, only a small part of the protein will adjust to a different conformation on the incoming ligand. The potential energy components are then preferably mapped in two parts. First the potential energy field grid is mapped for the larger part of the protein which does not change conformation, and this first grid is stored and reused each time. To calculate the total potential energy field grid for each conformation of the protein, the potential energy grid for the second part of the protein, which has assumed a different conformation, is calculated. The potential energy field grid of the first part is added to the potential energy grid of the second part to obtain the total potential energy field grid for the protein in the conformational state. This method of mapping the potential energy component grids is preferred because the computational time required to map the potential energy components onto the component grids is significant for larger molecules.

In the preferred embodiment, a limited forcefield restricted to electrostatic and Van der Waals interactions is used to describe the interaction between protein and ligand. The interaction enthalpy at time t is described by:

$$E_h(t) = E_e(t) + E_a(t) + E_r(t) \qquad \text{eq. 1}$$

in which $E_h$ is the enthalpy, $E_e$ the electrostatic component and $E_a$ and $E_r$ the attractive and repulsive Van der Waals components, respectively. Molecular dynamics can in principle find the configuration of a system for which the enthalpy is minimum. Boltzmann statistics, however, prohibit the answer to be found in a reasonable amount of time due to energy barriers unless there is some a priori knowledge of where the ligand might dock. Several developments have aimed at circumventing this problem by introduction of simplifying approximations. Most often, time dependence is replaced by a molecular mechanics approach of calculating the interaction enthalpy for different positions of the ligand relative to the protein. A priori knowledge of where the ligand might dock can reduce the number of calculations that have to be performed. Such a priori knowledge is however not available in most cases and a considerable computational effort is required to assess potential docking sites. In order to reduce the computational effort, it is proposed to make use of a method based on the Convolution Theorem. The reduction in computational effort makes possible calculations based on a dynamical description of protein-ligand interaction, and allows for calculations to be performed at sampling grid sizes of high resolution.

To first order approximation, dynamical motions of ligand and protein will be assumed to be uncorrelated. Eq. 1 can therefore be approximated by:

$$E_h(\bar{r}, f_p, f_s) = E_e(\bar{r}, f_p, f_s) + E_a(\bar{r}, f_p, f_s) + E_r(\bar{r}, f_p, f_s) \qquad \text{eq. 2}$$

in which $\bar{r}$ denotes the distance vector between protein and ligand, and $f_p$ is the set of coordinates, or frame, of the protein at time $t_p$ and $f_s$ the coordinate frame of the ligand at time $t_s$, $t_p$ and $t_s$ being uncorrelated. Since both protein and ligand are sampled independently over time, eq. 2 becomes separable in $f_p$ and $f_s$ and computations can be performed over $\{f_s\}$, one $f_p$ at a time. For simplicity it is assumed that there is only one set of coordinates $f_p$ for the protein structure.

In adiabatic dynamical simulations, i.e. when no external force is acting on a system of particles, the global velocity and global angular momentum of a system are constant and are reset to zero at the start of a simulation. Therefore, it is only possible to sample the relative atomic motions for 3N degrees of freedom instead of the usual 3N+6, where N is the number of atoms. Since rigid body translational sampling is implicitly incorporated in $\bar{r}$, eq. 2 must consequently be written explicitly in terms of rotational sampling utilizing Eulerian angles $\theta_1$, $\theta_2$, $\theta_3$:

$$E_h(\bar{r},\theta_1,\theta_2,\theta_3,f_s) = E_e(\bar{r},\theta_1,\theta_2,\theta_3,f_s) + E_a(\bar{r},\theta_1,\theta_2,\theta_3,f_s) + E_r(\bar{r},\theta_1,\theta_2,\theta_3,f_s) \qquad \text{eq. 3}$$

Eq. 3 can be further expanded in terms of atomic coordinates i and j of protein and ligand, respectively, as:

$$E_h(\bar{r}, \theta_1, \theta_2, \theta_3, f_s) = \sum_{i=0}^{N_P}\sum_{j=0}^{N_S} \frac{q_i q_j}{\epsilon_0 r_{ij}(\theta_1, \theta_2, \theta_3, f_s)} + \sum_{i=0}^{N_P}\sum_{j=0}^{N_S} \frac{A_{ij}}{r_{ij}^{12}(\theta_1, \theta_2, \theta_3, f_s)} - \sum_{i=0}^{N_P}\sum_{j=0}^{N_S} \frac{B_{ij}}{r_{ij}^{6}(\theta_1, \theta_2, \theta_3, f_s)} \qquad \text{eq. 4}$$

in which q is the atom partial charge, B and A the attractive and repulsive components of a (6–12) Lennard-Jones potential energy description, respectively. $N_p$ and $N_s$ denote the number of atoms in protein and ligand. Setting $A_{ij} = \sqrt{A_{ii}A_{jj}}$ and $B_{ij} = \sqrt{B_{ii}B_{jj}}$, all three terms in eq. 4 become separable:

$$E_h(\bar{r}, \theta_1, \theta_2, \theta_3, f_s) = \sum_{j=0}^{N_s} q_j \sum_{i=0}^{N_p} \frac{q_i}{\epsilon_0 r_{ij}(\theta_1,\theta_2,\theta_3,f_s)} + \sum_{j=0}^{N_s}\sqrt{A_{jj}}\sum_{i=0}^{N_p}\frac{\sqrt{A_{ii}}}{r_{ij}^{12}(\theta_1,\theta_2,\theta_3,f_s)} - \sum_{j=0}^{N_s}\sqrt{B_{jj}}\sum_{i=0}^{N_p}\frac{\sqrt{B_{ii}}}{r_{ij}^{6}(\theta_1,\theta_2,\theta_3,f_s)} \qquad \text{eq. 5}$$

Each of the three energy terms in eq. 5 can be interpreted as a series of discrete correlations in $\bar{r}_s$, with $\bar{r}_s \in \Re$, and s an instantiation of $\theta_1,\theta_2,\theta_3,f_s$.

To evaluate the interaction energy described in eq. 5, the protein structure must first be mapped onto a grid G. Each interaction energy term on the right hand side of eq. 5 is equivalent to a sum of products of two functions each of which can be evaluated separately: one function corresponding to calculation of the protein potential energy field on grid G while the second represents the ligand interaction field. For each grid point $\bar{g}$, the protein electrostatic potential energy $v_p^e$ described by the first term on the right hand side of eq. 5 becomes:

$$v_p^e(\bar{g}) = \sum_{i=0}^{N_p} \frac{q_i T(\bar{g}, r_i)}{\epsilon_0 |\bar{g} - r_i|} \qquad \text{eq. 6}$$

with T an interpolation function and $r_i$ the protein atom position of atom i. Mapping of the ligand component, which depends on s, onto grid G corresponds in eq. 5 to using a delta interpolation function such that for each grid point $\bar{g}(s)$ the ligand interaction field $\delta_s^e$ becomes:

$$\delta_s^e(\bar{g}(s)) = q_j T(\bar{g}(s), r_j(s)) \qquad \text{eq. 7}$$

with $r_j$ the atomic position of ligand atom j. Both second and third terms of eq. 5 representing the Van der Waals potential energy contribution can be similarly elaborated. Continuing, the estimated electrostatic contribution to the interaction enthalpy can then be written as:

$$\langle E_e(\bar{r}_s)\rangle = \sum_G \delta_s^e(\bar{g}(s)) v_p^e(\bar{r}_s + \bar{g}) \equiv \delta_s^e(\bar{g}(s)) \otimes v_p^e(\bar{g}) \qquad \text{eq. 8}$$

with $\otimes$ the correlation operator. Making use of the Convolution Theorem the identity on the right hand side of eq. 8 is equivalent to:

$$\delta_s^e(\bar{g}(s)) \otimes v_p^e(\bar{g}) = \Im^{-1}(\Delta_s^e(\bar{h}(s)) \cdot V_p^{*e}(\bar{h})) \qquad \text{eq. 9}$$

with $\Im$ denoting the discrete Fourier transformation (DFT) and $\Delta$ and $V$ the Fourier transformation of $\delta$ and $v$, respectively, and $\bar{h}$ a vector in spatial frequency domain; * indicates the complex conjugate. Eq. 9 is critical in the current approach in that it allows for a significant reduction of the computational effort from $O(N \times N)$ to $O(N\log_2 N)$ with N representing the number of grid points. Inclusion of Van der Waals dispersion energy terms is straightforward and consists of the addition to eq. 9 of two additional discrete Fourier transformations analogous to the electrostatic potential energy term.

The DFT algorithm inherently assumes the function being transformed to be a periodic function. To eliminate sampling end-effects due to overlap or cross-talk, the total number of grid points used to sample the ligand-protein forcefield must equal at least the sum of the grid dimensions used to represent the individual protein and ligand forcefield functions. Additionally, one should allow for a certain buffer as ligand size varies in $f_s$. In the present approach a representation is chosen that considers protein and ligand potential functions to be finite and non-periodic. Using the Convolution Theorem, interaction energy evaluation involves therefore Fourier decomposition to spatial frequency domain.

In principle the method can be implemented as a single 7-dimensional DFT (i.e. $\bar{r}_s, \theta_1, \theta_2, \theta_3, t_s$) or even higher dimensional space (if temperature, pH, etc. are included). Although this will reduce computational effort compared to a full 7-dimensional sequential row-column DFT approach, the approach will require large amounts of computer memory and will be unnecessarily computationally intensive. Since variables $\theta_1, \theta_2, \theta_3$ and $t_s$ refer to single, uncorrelated, instances of ligand conformation, computational effort can be reduced if each ligand conformation is treated separately. Efficiency of this approach can be illustrated as follows by considering for instance ligand conformational sampling as function of time in a dynamical simulation: if M samples of the ligand structure are recorded in time, then the total computational load for the evaluation of interaction energies using the Convolution Theorem will be of the order of $M*O(N\log_2 N)$, with N the total number of grid elements used in a 3-dimensional grid representation. Conversely, treating the same problem as a full 4-dimensional representation would involve a computational load of the order of $O(M*N\log_2(M*N))$, significantly larger than the former. Even with more elaborate implementations of higher dimensional FFT algorithms this difference is not diminished substantially. The present implementation uses therefore a sequential approach in $\theta_1, \theta_2, \theta_3, f_s$: each ligand instantiation is evaluated against the protein potential grid; thus terms describing protein interaction potentials (c.f. $v_p^e$ in eq. 6 for the electrostatic potential, and equivalent attractive and repulsive Van der Waals potentials), need only be calculated once and can be kept in the spatial frequency domain. Addition of terms takes place in spatial frequency domain. After back-transforming (eq. 8) a list of lowest minima is updated.

Since atomic positions are generally not congruent to grid elements an interpolation mechanism has been introduced as indicated in eq. 6 et seq. There are a number of schemes including Gaussian-, tri-linear- or spline interpolation. Gaussian interpolation scheme was chosen because it gives a better approximation than tri-linear interpolation. A spline interpolation was considered to be too elaborate for our purposes. Eq. 6 was consequently evaluated in two steps. If the numerator of eq. 6 is defined as:

$$Q_p(\bar{g}) = q_i T(\bar{g} - r_i) \qquad \text{eq. 10}$$

in which T now explicitly denotes a Gaussian interpolation function and $Q_p$ the protein charge distribution function, eq. 6 can be evaluated as:

$$v_p^e(\bar{g}) = \sum_{r_s} \frac{Q_p(\bar{r}_s)}{\epsilon_0|\bar{g} - \bar{r}_s|} = \frac{1}{\epsilon_0} Q_p(\bar{g}) * \frac{1}{|\bar{g}|} \qquad \text{eq. 11}$$

in which * denotes the convolution operator. The identity at the right hand side of eq. 11 can again be evaluated in spatial frequency domain according to the Convolution Theorem. The Gaussian interpolation scheme, applied to a 0.25 Å resolution grid, reproduces energies calculated analytically within 3 kcal/mol error. Similarly, eq. 7 becomes $\delta_s^e(\bar{g}(s)) = q_j T(\bar{g}(s) - r_j(s))$, with T explicitly denoting a Gaussian interpolation function and can be evaluated readily.

For calculations using fine grid sizes, evaluation of eq. 11 becomes impracticable. Though the convolution approach is faster than point by point evaluation, grid dimensions become too large for a reasonable sized computational platform. To circumvent this problem, an intermediate approach is preferred which consists of a two step calculation. First the ligand interaction energy with the entire protein is scanned at lower grid resolution typically 0.4–0.5 Å (referred to as global pattern calculation: considering the entire protein molecule) whereafter regions about lowest minima are selected for recalculation (see eq. 12 below) on a higher resolution grid typically 0.25 Å and displacing the ligand's center of mass within a volume of $11 \times 11 \times 11$ Å$^3$ around each minimum (local pattern calculation). Protein electrostatic forcefield contributions on finer grids were calculated according to:

$$v_p^e(\bar{g}) = \sum_{i=0}^{N_p} \frac{q_i}{\epsilon_0|\bar{g} - r_i|} \qquad \text{eq. 12}$$

Since evaluation of eq. 12 is no longer an interpolation, calculations become extremely accurate at high sampling grid resolution. The Van der Waals non-bonded interaction terms are treated similarly. No distance cutoff was applied in either method for potential function setup, c.f. eqs 11 and 12.

The implementation of the forcefield is generic in set up. Although CVFF force field was used throughout the calculations, other forcefields can be employed. The CVFF forcefield allows for intrinsic description of hydrogen bonds. Any explicit description of hydrogen bonding such as used in the AMBER force field can be implemented by modifying eq. 4 accordingly. The use of different power functions for the q, A and B term is also readily incorporated.

In order to have a forcefield parameterization independent measure of protein-ligand interactions or 'hits', the probability value p, based on the Boltzmann distribution was used where:

$$p(\bar{r}_s) = \frac{\exp\left(-\frac{<E(\bar{r}_s)>}{RT}\right)}{\sum_{r_s} \exp\left(-\frac{<E(\bar{r}_s)>}{RT}\right)} \qquad \text{eq. 13}$$

in which R is the molar gas constant and T the absolute temperature. This measure not only allows comparison of computational results between protein and ligand for different force fields but can also afford a measure of specific affinity by a ligand for a given binding site, allowing comparison of affinities among different ligands.

EXAMPLE

The above described method has been implemented using the computer program provided in the microfiche appendix, and tested as summarized herein below. All software was written in ANSI C++/C and has been successfully used on a SGI Indigo R4000 and a SGI Power Indigo R8000, both single CPU systems, and a CRAY Y-MP C90 used in single CPU mode. Available machine specific FFT routines have been used in order attain maximum computational speed. In case of the CRAY C90, the scalar version of the FFT routines were used. Where needed an interface to the FFT-PACK suite of FFT routines can be used.

MATERIALS AND METHOD

Predictive accuracy of the approach according to the invention was assessed using seven different protein-ligand complexes refined to high resolution (1.6–2.1 Å); coordinate files were obtained from the Brookhaven Protein Data Bank (PDB). The complexes examined were as follows: phospholipase $A_2$ complexed with a transition-state analog (1poe), β-trypsin complexed with benzamidine (3ptb), ribonuclease A complexed with cytidylic acid (1rob), lysozyme complexed with tri-N-acetylchitotriose (1hew), HIV1 protease complexed with U75875 inhibitor (1hiv), dihydrofolate reductase complexed with methotrexate (4dfr) and HIV1 protease complexed with XK263 inhibitor (1hvr).

Hydrogen atom generation

Prior to docking calculations hydrogen atom building was done using InsightII (TM of Biosym Technologies, San Diego) for all structures; unless indicated otherwise a pH of 7 was assumed during hydrogen atom generation. Partial charges and CVFF force field parameters were assigned using the BUILDER option in InsightII. Each ligand was energy minimized for 100 cycles using DISCOVER (TM of Biosym Technologies, San Diego). Protein coordinates were not allowed to vary during refinement. Except for lysozyme, protein-ligand interaction energies did not show improvement from their starting values. For lysozyme, a significant reduction in interaction energy of 54.2 kcal/mol was obtained and corresponded to an RMS shift of 1.16 Å by the ligand from its crystallographic determined coordinates. The translational shift in centers of mass between observed and calculated ligand positions was however only 0.04 Å suggesting imprecise ligand positioning, a consequence of unrelieved close hydrogen atom contacts. During all subsequent calculations, original crystallographic coordinates were used except for lysozyme where the refined coordinates were chosen.

Algorithm comparison

In order to compare the present Fourier method with other methods, two different computational algorithms were implemented which yielded identical interaction energy values. The first involved a straightforward atom-to-atom energy calculation, based on charge-charge and Van der Waals energy contributions. This implementation, in which the computational load is dependent on the number of atoms in both protein and ligand, was optimized as to minimize the number of multiplications. The second algorithm was based on an atom-to-grid method, were the protein potential functions for electrostatic and Lennard-Jones contributions were mapped onto a 0.25 Å resolution sampling grid prior to energy calculations. In this implementation, the computational load is dependent only on the number of ligand atoms and was also optimized as to minimize the number of multiplications, ligand atomic positions were subjected to the Gaussian interpolation scheme described above. For both algorithms, and similar to the fast Fourier method, no distance cutoff was applied during calculations. Comparisons represented identical number of configurations for protein-ligand complexes of HIV/U75875, LYS/NAG, FOLATE/MTX and TRYP/BEN.

RESULTS

Docking site determination

In order to minimize bias, ligand starting positions were randomized prior to calculation in orientation and translation with respect to the target protein. High computational memory demands required that each ligand-protein complex be analyzed using the two-step evaluation procedure described above. All possible protein-ligand binding sites were first explored at 0.5 Å grid size resolution from which lowest minima were extracted for local exploration at 0.25 Å grid size resolution. Shown in Table 1a is a comparison between the crystallographic determined structures and nearest corresponding minima for complexes which could be successfully determined using a randomized starting orientation and translation of the ligand. Also indicated are Euler sampling and relative ranking of the minima used in comparison with the crystallographic determined structure. Repeated calculations did not show differences as to the ranking of the minima in the cases of HIV/U75875, LYS/NAG and TRYP/BEN. In the case of the RNASE/CYT complex repeated calculations did show differences in peak rank of the nearest corresponding minima and are also shown in Table 1a. As discussed below these multiple calculations, using different randomized starting conditions, were used to further examine energetically similar conformations and enabled unique identification of one best ranking peak based on the resealing property of Boltzmann statistics.

Calculations for three complexes in which the ten lowest minima failed to predict ligand's center of mass to within one bond length of the ligand's crystallographic center of mass were repeated without randomization of the ligand's starting position. In all three cases, successful predictions were obtained coinciding to within one bond length of respective centers of mass of the crystallographically determined structures. Results are shown in Table 1b.

TABLE 1a

Protein-ligand docking of four crystallographically determined complexes using a 0.25 Å grid size interval, applying Euler sampling with translational and rotational randomization of ligand's starting position.

| protein-ligand complex | Euler sampling interval (°) | $r^1$ | $d (\text{Å})^2$ | $\theta (°)^3$ |
|---|---|---|---|---|
| HIV/U75875 | 20 | 1 | 1.11 | 8.0 |
| LYS/NAG | 30 | 1 | 0.47 | 6.8 |
| TRYP/BEN | 45 | 1 | 0.55 | 14.8 |
| RNASE/CYT$^4$ | 12 | $1 (1)^5$ | 0.90 | $21.4^6$ |
| RNASE/CYT | 12 | $1 (2)^5$ | 0.98 | 23.8 |
| RNASE/CYT | 12 | $2 (3)^5$ | 0.91 | 21.9 |
| RNASE/CYT | 12 | $4 (4)^5$ | 0.75 | 19.4 |

TABLE 1b

Protein-ligand docking of three crystallographically determined complexes using a 0.25 Å grid size interval without translational and rotational randomization of ligand's starting position.

| protein-ligand complex | Euler sampling interval (°) | $r^1$ | $d (\text{Å})^2$ | $\theta (°)^{3,8}$ |
|---|---|---|---|---|
| FOLATE/MTX | 20 | 1 | $0 (0.23)^7$ | 0 |
| PLA2/GEL | 45 | 1 | $0.25 (0.19)^7$ | 0 |
| HIV/XK263 | 45 | 1 | $0.25 (0.10)^7$ | 0 |

[1] r defines the rank of the interaction energy relative to the lowest calculated global minimum and corresponding to the protein ligand complex whose center of mass calculated closest to that of the crystallographically observed complex.
[2] translational shift δ was defined as the distance between the centers of mass of predicted and observed protein-ligand complexes.
[3] rotational shift θ was obtained from the trace of the rotation matrix of the transformation operation relating calculated ligand position and observed ligand position in the protein-ligand complex: Tr[R] = 2cos θ + 1, with θ the rotation angle.
[4] in the case of RNASE/CYT complexes, the most probable docking site was selected based on Boltzmann statistics from the calculations listed (see also text).
[5] shown in parenthesis are the relative ranking in interaction energy of the RNASE/CYT complexes.

TABLE 1b-continued

Protein-ligand docking of three crystallographically determined complexes using a 0.25 Å grid size interval without translational and rotational randomization of ligand's starting position.

| protein-ligand complex | Euler sampling interval (°) | $r^1$ | $d$ (Å)$^2$ | $\theta$ (°)$^{3,8}$ |
|---|---|---|---|---|

[6] rotational shift of the predicted RNASE/CYT complex is larger than the actual Euler sampling interval and is a consequence of mapping atoms to a finite grid.
[7] shown in parenthesis are translational shifts obtained from comparative calculations using only translational randomization of ligands' starting positions.
[8] zero values are in fact expected as no rotational randomization was applied and indicated that no false minima were obtained from the set of tested configurations.

Resolution Dependency

Protein ligand complexes shown in Table 1a which were predicted using randomized ligand's starting positions were further assessed as a function of grid size resolution dependency. Calculations were performed at 2.0 Å, 1.0 Å, 0.7 Å, 0.5 Å, 0.4 Å, and 0.25 Å grid size resolution, respectively (Table 2). Due to memory limitations only local pattern calculations were performed around the crystallographic observed structures for resolutions of 0.4 Å and 0.25 Å. Repeated calculations using different randomized starting conditions for the ligands in the above cases did not show any significant changes in the results shown in Table 2.

TABLE 2

Resolution dependency of protein-ligand complex prediction.

| | Resolution (Å) | | | | | | | | | | |
|---|---|---|---|---|---|---|---|---|---|---|---|
| | global | | | | | | | local | | | |
| protein-ligand | 2.0 | | 1.0 | | 0.7 | | 0.5 | | 0.4 | | 0.25 | |
| complex$^1$ | $\delta^3$ | $r^2$ | $\delta$ | r | $\delta$ | r | $\delta$ | r | $\delta$ | r | $\delta$ | r |
| RNASE/CYT | 15.7 | 64 | 7.3 | 63 | 4.9 | 2 | 1.8 | 20 | 1.7 | 2 | 1.0 | 1 |
| HIV/U75875 | 21.1 | 16 | 17.8 | 85 | 12.2 | 67 | 8.0 | 67 | 3.6 | 9 | 1.1 | 1 |
| LYS/NAG | 21.0 | 87 | 16.0 | 57 | 5.7 | 47 | 3.0 | 25 | 0.4 | 2 | 0.5 | 1 |
| TRYP/BEN | 24.1 | 85 | 14.4 | 75 | 7.3 | 59 | 6.0 | 8 | 0.9 | 8 | 0.5 | 1 |

[1] calculations were performed using a randomized starting orientation/translation of the observed ligand structure.
[2] rank of interaction energy minimum defined as in table 1.
[3] translational shift $\delta$ defined as in table 1.

Dynamical docking calculations

In order to test the methodology using a dynamical description of ligand, the TRYP/BEN complex was examined. A series of frames were generated corresponding to an in vacuo dynamical simulation of the ligand at 300° K. for 1.2 ps at 1.0 fs step intervals and frames sampled every 50 steps. The resulting 23 frames, one of which corresponded to the crystallographic solution, were used as input for interaction energy calculation. Frames depict essentially a 180° rotation of the amidino group with respect to the phenyl moiety of benzamidine. Each frame was evaluated using a Euler sampling interval of 45° on a grid of 0.25 Å resolution. The resulting 5 lowest minima are shown in table 3. Column 7 in table 3 shows the minima ranking after correction for the difference in ligand internal energy (column 5) between that of the in vacuo simulation and that calculated for the crystallographic structure, differences in ligand internal energy being a consequence of conformational strain introduced by the simulation.

TABLE 3

Docking of Trypsin-benzamide complex using a dynamical$^1$ ligand description

| initial ranking | $d$ (Å) | $\theta$ (°) | $E_{enthalpy}$ kcal/mol | $\Delta E_{con}^2$ kcal/mol | $E_{tot}$ kcal/mol | final ranking |
|---|---|---|---|---|---|---|
| 1 | 1.68 | 172 | −40.09 | 16.01 | −24.08 | 10 |
| 2 | 2.04 | 139 | −36.12 | 8.29 | −27.83 | 8 |
| 3 | 0.25 | 2 | −35.90 | 10.53 | −25.37 | 9 |
| 4 | 0.354 | 0 | −35.66 | 0.0 | −35.66 | 1 |
| 5 | 0.354 | 0 | −35.60 | 0.0 | −35.60 | 2 |

[1] based on 23 frames sampled over 1.2 ps.
[2] ligand internal energy difference corresponding to conformational strain calculated relative to the crystallographic ligand conformation.

Computational load

Computations were performed on three different platforms. Table 4 summarizes CPU times utilized for each of the 10 non-similar calculations listed in Tables 1a, 1b and 3. The times listed are without the overhead calculation time needed for the potential function setup.

TABLE 4

CPU time for local pattern calculations using 0.25 Å grid resolution

| complex | grid size | no. of orientations | platform | CPU-time |
|---|---|---|---|---|
| FOLATE/MTX | 118 × 118 × 118 | 612 | R8000 | 16h7 |
| HIV/U75875 | 146 × 145 × 145 | 612 | R8000 | 27h46 |
| LYS/NAG | 132 × 132 × 132 | 112 | C90 | 1h42 |
| LYS/NAG | 132 × 132 × 132 | 264 | R8000 | 4h1 |
| PLA2/GEL | 112 × 111 × 111 | 112 | R4000 | 3h30 |
| RNASE/CYT | 84 × 84 × 84 | 1740 | R8000 | 9h27 |
| TRYP/BEN | 80 × 80 × 80 | 24 | C90 | 5m9 |
| TRYP/BEN | 80 × 80 × 80 | 112 | R4000 | 1h9 |

TABLE 4-continued

CPU time for local pattern calculations using 0.25 Å grid resolution

| complex | grid size | no. of orientations | platform | CPU-time |
|---|---|---|---|---|
| TRYP/BEN (dyn) | 80 × 80 × 80 | 2352 | R4000 | 10h8 |
| HIV/XK263 | 142 × 141 × 141 | 112 | R8000 | 4h54 |

To assess gain in computational speed, CPU times of the present fast Fourier transform method were compared with results of identical computations using atom-to-atom and atom-to-grid algorithms described above. For four protein-ligand complexes, of different computational complexity in terms of the sampling grid size used, the last column in Table 5 lists the CPU computation times corresponding to each algorithm. Computations involved calculations with a 30° Euler sampling interval using a 0.25 Å resolution sampling grid placed within a 11×11×11 Å box and centered around the respective ligands' crystallographic positions. Also indicated are sampling grid size and number of atoms. In cases of atom-to-atom and atom-to-grid computations, CPU times listed were obtained by extrapolation based on sample calculations corresponding to one hundred ligand conformations.

DISCUSSION OF EXAMPLE

Docking site determination

The present method is able to reproduce the crystallographic observed liganded complexes with a high rate of success. A result was considered successful when the translational difference between calculated and crystallographically observed ligand's center of mass was less than one carbon-carbon bond length. Except for two calculations in case of the RNASE/CYT complex discussed below, the lowest energy minimum of each protein-ligand complex, shown in Table 1a, coincided with the crystallographic structure to within less than one bond length. Local pattern calculations for the RNASE/CYT complex (Table 1a) showed, contrary to other interaction energy calculations, minima with only slight differences in binding energy ($\leq 6$ kcal/mol). Two of the predicted centers of mass were decidedly different from crystallographic observed complexes suggesting that predictive accuracy may be dependent on starting position randomization. The lowest interaction energy for the RNASE/CYT complex calculations corresponded nevertheless to the predicted center of mass having the least difference, 0.90 Å, with respect to that of the crystallographic complex. Center of mass of the second minimum differed by 0.98 Å from the crystallographic structure while the two latter minima predicted a center of mass more than 2 Å from the crystallographic complex. Energy differences between the lowest interaction energy minimum and remaining minima corresponded to 2.2 kcal/mol, 3.0 kcal/mol and 5.4 kcal/mol while Boltzmann probabilities for each minimum, calculated according to eq. 13, were 0.92, 0.54, 0.39 and 0.29 respectively and are insufficient for order of magnitude minima discrimination typically observed in the other protein-ligand complexes. To enhance global minimum discrimination, interaction energies of the four calculations were appropriately summed and Boltzmann probabilities recalculated. Minima ranking following recalculation yielded a probability of 0.89 for the lowest minimum and which corresponded to the previous global minimum. Boltzmann probability for the first predicted protein-ligand complex not coincident with the crystallographic observed structure and now ranking third was 0.005. Summation of repeated interaction energy calculations thus afforded improved discrimination of the predicted crystallographic complex by nearly two orders of magnitude. In general, choice of the true docking site amongst alternate sites is largely dependent on the energy difference among docking sites. Cumulative Boltzmann probabilities from repeated calculations with random starting positions can be used to accurately discriminate the true docking site in cases where it can not be distinguished solely from energy differences.

In three of the seven selected complexes, docking calculations apparently failed to predict the crystallographic solution when a full randomized starting positions were employed; without translational and rotational randomization, however, the crystallographic solutions were unequivocally obtained and corresponded to the expected Euler sampling angle of zero degrees (Table 1b). Translational randomization at 0.25 Å resolution also reproduced the crystallographic solutions (data not shown). The seeming failure to predict the crystallographic solution from a full randomized starting position is apparent if one considers the 'tightness of fit' of these ligands at their target site. In order to reproduce the crystallographic solution using randomized starting coordinates, exploration using a 1°–2° Euler sampling interval would be required. The FOLATE/MTX and PLA2/GEL complexes show similar tight fitting energy profiles (not shown) requiring a Euler sampling interval in the order of 4°–5° for adequate minimum exploration. Currently, the Euler sampling interval cannot be less than 12° due to computational limitations. The fact that the non-randomized calculations reproduced the crystallographic solution unequivocally suggests that for a Euler sampling interval of less than 12°, a successful solution should be obtained using randomized starting position. Increasing the Euler sampling interval should also improve agreement between predicted and crystallographically observed protein-ligand complexes in aforementioned calculations that employed randomized starting coordinates (Table 1a).

Resolution dependency

From table 2, it is evident that calculations at fine grid size resolution are essential for obtaining agreement with the crystallographic observed complexes. At low grid size resolution (>0.7 Å) the sampled energy surface was essentially flat and no definitive energy minima could be discerned. At higher resolutions (0.7 Å–0.4 Å) the predicted centers of mass approached the observed structure; the grid, however, was sampled still too coarse as the calculated energy corresponding to the crystallographic observed complex was still too high (i.e. ranking relative to lowest minima). At high resolution (0.25 Å) differences between centers of mass were least and lowest energy minima for docked ligands reflected the crystallographic observed structures. Conversely, low resolution calculations without randomization of the ligand's starting conditions, equivalent to extremely fine Euler sampling, show the same 'flat' energy surfaces as with randomized starting positions (calculations not shown). These results suggest that putative binding sites can only be predicted using high resolution calculations, <0.4 Å grid size. A previous report (Vakser I. A., Protein docking for low-resolution structures, Protein Eng. 8(4):371–377, 1995) using 7.0 Å grid size resolution and employing a shape complementary approach obtained statistically reasonable results in centers of mass prediction. It should be noted, however, that for this method to be generally successful the shape and size of the ligand must show significant features resolvable at 7.0 Å resolution.

Dynamical docking calculations

Results of the TRYP/BEN complex using a dynamical description for the benzamidine molecule (Table 3) shows the crystallographically observed structure among the highest ranking solutions. Allowance for ligand conformational strain introduced by the dynamical simulation modifies the rank order of the solutions such that the crystallographic structure corresponds to the two highest ranking solutions and the three previous lowest minima are now ranked 8th, 9th and 10th, respectively. The top ranking structures show the phenyl ring of benzamide in approximately identical orientations, underscoring the importance of the hydrophobic interaction between the phenyl moiety of benzamidine and trypsin.

Computational load

Evaluation of the interaction energies corresponding to the large numbers of ligand conformations in a protein-ligand complex, the present method represents a considerable gain in computational speed. With respect to the direct sum computation of correlations as expressed at the right hand side in eq. 8., considerable improvement in computational speed was gained using the FFT approach, which is $O(Nlog_2 N)$ rather than $O(N \times N)$ in terms of the number of operations performed where N represents the number of grid elements. Computations for each of the cases, shown in Table 5, corresponded to interaction energies calculated for 22,488,576 different configurations, and based on the CPU times required for each computation, it is evident that the present method is superior with respect to atom-to-atom and atom-to-grid computations.

TABLE 5

CPU times for different computational algorithms

| protein-ligand complex | evaluation method | grid size | computational time |
|---|---|---|---|
| HIV/U75875 | atom-to-atom[2] | $N_p = 1561^5$, $N_s = 121^6$ | 179.6 days |
| | atom-to-grid[3] | $N_s = 121$, $44 \times 44 \times 44$ | 47.4 days |
| | FFT[4] | $146 \times 145 \times 145$ | 27.7 hours |
| LYS/NAG | atom-to-atom | $N_p = 1960$, $N_s = 84$ | 212.8 days |
| | atom-to-grid | $N_s = 84$, $44 \times 44 \times 44$ | 33.0 days |
| | FFT | $132 \times 132 \times 132$ | 4.0 hours |
| FOLATE/MTX | atom-to-atom | $N_p = 2441$, $N_s = 57$ | 179.8 days |
| | atom-to-grid | $N_s = 57$, $44 \times 44 \times 44$ | 22.3 days |
| | FFT | $118 \times 118 \times 118$ | 6.9 hours |
| TRYP/BEN | atom-to-atom | $N_p = 3219$, $N_s = 17$ | 71.3 days |
| | atom-to-grid | $N_s = 17$, $44 \times 44 \times 44$ | 6.6 days |
| | FFT | $80 \times 80 \times 80$ | 1.2 hours |

[1]Interaction energies were calculated at 0.25 Å resolution, within a box of 11 × 11 × 11 Å³ about the substrate's crystallographic position, using 30° Euler sampling (22,488,576 ligand conformations) on a single CPU SGI R8000 platform.
[2]Atom-to-atom interaction energy evaluation; indicated CPU time values are extrapolated from a sample of 100 calculated conformations. Algorithm optimized for multiplicative efficiency.
[3]Protein potential function was sampled on 0.25 D grid prior to energy evaluation; indicated CPU times exclude potential function setup and are extrapolated from a sample of 100 conformations calculated. Ligand atomic positions were interpolated by Gaussian interpolation. Algorithm optimized for multiplicative efficiency.
[4]Proposed method.
[5]$N_p$ represents number of atoms in protein molecule.
[6]$N_s$ represents number of atoms in ligand molecule.

The method according to the invention is robust in nature. In the above example, of seven protein-ligand complexes, the crystallographic solution was successfully reproduced. In four of the seven studies, good agreement could be obtained using an unbiased approach. Due to the relatively tight fit of ligand in its binding site in the remaining three cases, the crystallographic observed complex failed to be reproduced from randomized starting position of the ligand, whereas no randomization yielded success. This apparent failure suggest that accurate prediction using randomized starting positions can be obtained with a finer Eulerian sampling interval than the current minimum of 12°.

Boltzmann probabilities represent an useful tool to discriminate against artefactual docking sites. In the case of RNASE/CYT complex, four calculations at 0.25 Å grid size resolution showed that two of four highest ranking peaks did not predict the crystallographic observed complex, although the highest ranking peaks for each calculation had energies that were similar to within 6 kcal/mol. Combined Boltzmann probabilities clearly identified the lowest energy minimum as corresponding to the crystallographic observed complex. Boltzmann probabilities calculated by summation of interaction energies represents a useful tool to improve certitude of predicted docking sites.

Remarkably, without any explicit parameterization to take solvation into account, all seven test cases yielded unambiguously the crystallographic solution. The high success in reproducing all crystallographic observed structures suggests enthalpy of formation is decisive in determining observed complex stability in case of the selected protein-ligand structures.

The analysis clearly indicates that for predictive accuracy quantitative calculations should be performed at least at 0.4 Å grid size resolution. Satisfactory results are obtained at 0.25 Å resolution. The two-step computational procedure used in our approach: calculation at 0.4 Å resolution, selection of lowest minima, followed by a series of local calculations about lowest minima at 0.25 Å resolution is in principle not needed. A single calculation at 0.25 Å resolution is preferred. Computational resources may impose, however, a two-step procedure.

A dynamical description of protein-ligand complex formation has been demonstrated for the TRYP/BEN complex. Although only a dynamical description for ligand was used, a combined protein ligand dynamical description would be equivalent to successive calculations of the protein/ligand complex each corresponding to a different conformational state of the protein. The additive nature of the potential functions allows a judicious approach in potential function setup thus saving overall computation time.

The present invention may be used in predicting putative ligand binding sites. Although the method according to the invention is superior, considering computational load, compared to similar methods of calculating protein-ligand interaction enthalpies, a considerable improvement is expected when the program is ported to a vector/parallel computational platform. The method and especially the FFT routine which is at the heart of the method is inherently suitable for vectorization and parallel computing. In addition, calculation of interaction energies as a function of Eulerian angles $(\theta_1, \theta_2, \theta_3)$ or conformation $(t_s)$ can be performed in parallel. With the imminent availability of larger computer memories, combined with computer vectorization and parallelism at desk-top level, the methodology should become suitable even for calculations on large protein/ligand complexes including protein-protein interactions.

What is claimed is:

1. A method for generating a position value for an energetically favorable binding site between two molecules, comprising the steps of:

a) obtaining potential energy structural data for each atom site in said molecules;

b) selecting a grid resolution corresponding to a sampling grid size less than 0.45Å;

c) selecting a range of relative rotations between said two molecules;

d) mapping a plurality of potential energy field components of one of said molecules onto a corresponding one of a plurality of energy field component grids having said resolution with said one molecule at a predetermined rotation and position, wherein each grid point of said component grids has a potential energy value interpolated from said potential energy structural data;

e) mapping a plurality of interaction field components of the other of said two molecules onto a corresponding one of a plurality of interaction component grids having said resolution with said other molecule at a predetermined rotation and position, said interaction field component corresponding to coefficients of a force field between said molecules, wherein each grid point of said component grids has an interaction field value interpolated from said potential energy structural data;

f) calculating a transform of each said potential energy field component grid and of each said interaction field component grid, calculating a function of said transformed grids, and using an inverse transform on a result of said function to obtain a correlation between each said potential energy field component grid and each said interaction field grid and to obtain a grid of molecule binding energy values representing a binding energy of said two molecules in said relative rotation for relative translational positions in space between said molecules;

g) determining at least one maximum of said binding energy values and recording said relative translational positions for said maximum binding energy values;

h) rotating at least one of said molecules according to each said relative rotation in said range, repeating said step of mapping for said at least one of said molecules and subsequently repeating said steps (f) and (g) of calculating and determining for each said relative rotation; and i) selecting an energetically favorable one of said relative rotations in said range and said relative translational positions based on said maximum binding energy values to generate said position value for an energetically favorable binding site between said two molecules.

2. The method according to claim 1, wherein said at least one of said molecules rotated is said other molecule only, whereby said interaction field component grid is mapped for each rotation of said other molecule and computation time is reduced.

3. The method according to claim 1, wherein said step of calculating a correlation comprises calculating a discrete Fourier transform of said component grids, calculating a product of said transformed grids, and using an inverse Fourier transform to obtain said grid of molecule binding energy values.

4. The method according to claim 2, wherein said step of calculating a correlation comprises calculating a discrete Fourier transform of said component grids, calculating a product of said transformed grids, and using an inverse Fourier transform to obtain said grid of molecule binding energy values.

5. The method according to claim 1, wherein said step of selecting said energetically favorable one of said relative rotations and translational positions comprises selecting a plurality of most energetically favorable ones of said maximum binding energy values, and calculating Boltzmann probabilities of occupying energy states corresponding to said plurality of most energetically favorable ones of said maximum binding energy values, said energetically favorable one of said relative rotations and translational positions selected corresponding to a rotation and translational position of one of said plurality of most energetically favorable ones of said maximum binding energy values having a highest one of said Boltzmann probabilities calculated.

6. The method according to claim 2, wherein said step of selecting said energetically favorable one of said relative rotations and translational positions comprises selecting a plurality of most energetically favorable ones of said maximum binding energy values, and calculating Boltzmann probabilities of occupying energy states corresponding to said plurality of most energetically favorable ones of said maximum binding energy values, said energetically favorable one of said relative rotations and translational positions selected corresponding to a rotation and translational position of one of said plurality of most energetically favorable ones of said maximum binding energy values having a highest one of said Boltzmann probabilities calculated.

7. The method according to claim 3, wherein said step of selecting said energetically favorable one of said relative rotations and translational positions comprises selecting a plurality of most energetically favorable ones of said maximum binding energy values, and calculating Boltzmann probabilities of occupying energy states corresponding to said plurality of most energetically favorable ones of said maximum binding energy values, said energetically favorable one of said relative rotations and translational positions selected corresponding to a rotation and translational position of one of said plurality of most energetically favorable ones of said maximum binding energy values having a highest one of said Boltzmann probabilities calculated.

8. The method according to claim 4, wherein said step of selecting said energetically favorable one of said relative rotations and translational positions comprises selecting a plurality of most energetically favorable ones of said maximum binding energy values, and calculating Boltzmann probabilities of occupying energy states corresponding to said plurality of most energetically favorable ones of said maximum binding energy values, said energetically favorable one of said relative rotations and translational positions selected corresponding to a rotation and translational position of one of said plurality of most energetically favorable ones of said maximum binding energy values having a highest one of said Boltzmann probabilities calculated.

9. The method according to claim 1, wherein said grid resolution selected is a lower grid resolution, and said position value generated is a coarse position value, further comprising steps of:

selecting a fine grid resolution higher than said lower grid resolution;

selecting a fine range of relative rotations between said two molecules proximate to a rotation value of said position value;

repeating said steps (d) through (i) for said fine grid resolution and for said fine range to generate said position value, whereby computation speed may be increased by using a lower grid resolution to obtain said coarse position value, and grid mapping at said fine resolution may be done using smaller grid dimensions while obtaining a more accurate final position value.

10. The method according to claim 2, wherein said grid resolution selected is a lower grid resolution, and said position value generated is a coarse position value, further comprising steps of:

selecting a fine grid resolution higher than said lower grid resolution;

selecting a fine range of relative rotations between said two molecules proximate to a rotation value of said position value;

repeating said steps (d) through (i) for said fine grid resolution and for said fine range to generate said position value, whereby computation speed may be increased by using a lower grid resolution to obtain said coarse position value, and grid mapping at said fine resolution may be done using smaller grid dimensions while obtaining a more accurate final position value.

11. The method according to claim 3, wherein said grid resolution selected is a lower grid resolution, and said position value generated is a coarse position value, further comprising steps of:

selecting a fine grid resolution higher than said lower grid resolution;

selecting a fine range of relative rotations between said two molecules proximate to a rotation value of said position value;

repeating said steps (d) through (i) for said fine grid resolution and for said fine range to generate said position value, whereby computation speed may be increased by using a lower grid resolution to obtain said coarse position value, and grid mapping at said fine resolution may be done using smaller grid dimensions while obtaining a more accurate final position value.

12. The method according to claim 4, wherein said grid resolution selected is a lower grid resolution, and said position value generated is a coarse position value, further comprising steps of:

selecting a fine grid resolution higher than said lower grid resolution;

selecting a fine range of relative rotations between said two molecules proximate to a rotation value of said position value;

repeating said steps (d) through (i) for said fine grid resolution and for said fine range to generate said position value, whereby computation speed may be increased by using a lower grid resolution to obtain said coarse position value, and grid mapping at said fine resolution may be done using smaller grid dimensions while obtaining a more accurate final position value.

13. The method according to claim 5, wherein said grid resolution selected is a lower grid resolution, and said plurality of most energetically favorable ones of said maximum binding energy values are coarse values, further comprising steps of:

selecting a fine grid resolution higher than said lower grid resolution;

selecting a plurality of fine ranges of relative rotations between said two molecules proximate to a rotation value corresponding to each of said plurality of most energetically favorable ones of said maximum binding energy values; and repeating said steps (d) through (i) for said fine grid resolution and for each of said fine ranges to obtain a fine plurality of most energetically favorable ones of said maximum binding energy values for calculating said Boltzmann probabilities, whereby computation speed may be increased by using a lower grid resolution to obtain said coarse position value, and grid mapping at said fine resolution may be done using smaller grid dimensions while obtaining a more accurate final position value.

14. The method according to claim 6, wherein said grid resolution selected is a lower grid resolution, and said plurality of most energetically favorable ones of said maximum binding energy values are coarse values, further comprising steps of:

selecting a fine grid resolution higher than said lower grid resolution;

selecting a plurality of fine ranges of relative rotations between said two molecules proximate to a rotation value corresponding to each of said plurality of most energetically favorable ones of said maximum binding energy values; and repeating said steps (d) through (i) for said fine grid resolution and for each of said fine ranges to obtain a fine plurality of most energetically favorable ones of said maximum binding energy values for calculating said Boltzmann probabilities, whereby computation speed may be increased by using a lower grid resolution to obtain said coarse position value, and grid mapping at said fine resolution may be done using smaller grid dimensions while obtaining a more accurate final position value.

15. The method according to claim 7, wherein said grid resolution selected is a lower grid resolution, and said plurality of most energetically favorable ones of said maximum binding energy values are coarse values, further comprising steps of:

selecting a fine grid resolution higher than said lower grid resolution;

selecting a plurality of fine ranges of relative rotations between said two molecules proximate to a rotation value corresponding to each of said plurality of most energetically favorable ones of said maximum binding energy values; and repeating said steps (d) through (i) for said fine grid resolution and for each of said fine ranges to obtain a fine plurality of most energetically favorable ones of said maximum binding energy values for calculating said Boltzmann probabilities, whereby computation speed may be increased by using a lower grid resolution to obtain said coarse position value, and grid mapping at said fine resolution may be done using smaller grid dimensions while obtaining a more accurate final position value.

16. The method according to claim 8, wherein said grid resolution selected is a lower grid resolution, and said plurality of most energetically favorable ones of said maximum binding energy values are coarse values, further comprising steps of:

selecting a fine grid resolution higher than said lower grid resolution;

selecting a plurality of fine ranges of relative rotations between said two molecules proximate to a rotation value corresponding to each of said plurality of most energetically favorable ones of said maximum binding energy values; and repeating said steps (d) through (i) for said fine grid resolution and for each of said fine ranges to obtain a fine plurality of most energetically favorable ones of said maximum binding energy values for calculating said Boltzmann probabilities, whereby computation speed may be increased by using a lower grid resolution to obtain said coarse position value, and grid mapping at said fine resolution may be done using smaller grid dimensions while obtaining a more accurate final position value.

17. The method according to claim 1, wherein said energy field components comprise a electrostatic component and Van der Waals components.

18. The method according to claim 17, wherein said Van der Waals components comprise a $10^{-6}$ component and a $10^{-12}$ component.

19. The method according to claim 1, wherein said grid resolution is different for different ones of said field components, whereby those field components having a function which is more sensitive to position can be calculated at a higher grid resolution.

20. The method as claimed in claim 1, wherein at least one of said steps (d) and (e) is repeated for at least one different conformation of at least one of said molecules, and said steps (f) through (i) are repeated for said at least one different conformation.

21. The method as claimed in claim 20, wherein a larger non-conformed portion of said one molecule in said at least one different conformation is not remapped, while the remaining smaller conformed portion is remapped.

22. The method as claimed in claim 2, wherein said one molecule is a protein and said other molecule is a ligand.

23. The method as claimed in claim 1, wherein said grid size is about 0.25Å.

24. The method as claimed in claim 9, wherein said fine grid resolution has a size of about 0.25Å.

* * * * *